United States Patent [19]
Yeamans

[11] Patent Number: 5,714,696
[45] Date of Patent: Feb. 3, 1998

[54] FLUID SAMPLING APPARATUS AND METHOD

[75] Inventor: David R. Yeamans, Los Alamos, N. Mex.

[73] Assignee: The Regents of the University of California, Oakland, Calif.

[21] Appl. No.: 663,372

[22] Filed: Jun. 13, 1996

Related U.S. Application Data

[63] Continuation of Ser. No. 498,959, Jul. 6, 1995, abandoned.

[51] Int. Cl.⁶ ............................................. G01N 1/00
[52] U.S. Cl. ............................................. 73/863.84
[58] Field of Search ........................ 73/863.83, 863.84, 73/864.11, 864.15, 864.21, 864.34, 864.35, 864.62, 864.63, 864.81, 864.83–864.85, 864.87, 864.91

[56] References Cited

U.S. PATENT DOCUMENTS

| | | |
|---|---|---|
| 3,754,434 | 8/1973 | Guild. |
| 3,866,474 | 2/1975 | Hasselmann ................... 73/421.5 R |
| 3,886,800 | 6/1975 | Boehringer ................... 73/421.5 R |
| 3,938,391 | 2/1976 | Winkler ....................... 73/421.5 R |
| 3,950,136 | 4/1976 | Bellinga ........................... 23/232 R |
| 4,056,981 | 11/1977 | Kalka et al. ..................... 73/864.91 |
| 4,195,524 | 4/1980 | Hansen ......................... 73/421.5 R |
| 4,208,372 | 6/1980 | Huber ................................... 422/65 |
| 4,296,071 | 10/1981 | Weiss et al. ..................... 73/864.11 |
| 4,484,017 | 11/1984 | Kenton. |
| 4,638,674 | 1/1987 | Redmann ......................... 73/863.12 |
| 4,750,373 | 6/1988 | Shapiro ............................ 73/864.87 |
| 5,183,486 | 2/1993 | Gatten et al.. |

Primary Examiner—Robert Raevis
Attorney, Agent, or Firm—Gemma Morrison Bennett; William A. Eklund

[57] ABSTRACT

Incorporation of a bellows in a sampling syringe eliminates ingress of contaminants, permits replication of amounts and compression of multiple sample injections, and enables remote sampling for off-site analysis.

3 Claims, 3 Drawing Sheets

FLUID SAMPLING APPARATUS AND METHOD

This application is a continuation of Ser. No. 08/498,959, filed Jul. 6, 1995, and now abandoned.

This invention was made with government support under Contract No. W-7405-ENG-36 awarded by the U.S. Department of Energy. The government has certain rights in the invention.

TECHNICAL FIELD

This invention relates to fluid sampling technology and devices.

BACKGROUND ART

There is a need for ways of sampling fluids for analytical purposes without introduction of contaminants, particularly when detection of very low concentrations of components is necessary. Several techniques and apparatuses for gas sampling have been used in attempts to obtain samples uncontaminated by impurities from the air.

Conventional syringes have been used to draw gas samples through ports, septa or diaphragms of various sorts. Other sampling devices include bags hermetically sealed in vacuum containers (U.S. Pat. No. 3,866,474); sealed crushable, puncturable tubes with removable pistons (U.S. Pat. No. 3,886,800); sample receiving containers in compressed gas vessels (U.S. Pat. No. 3,938,391); containers that are cooled to create partial vacuums to draw environmental gases into the containers (U.S. Pat. No. 4,195,524); and sample collecting systems in which pumps are used to propel gases through precipitate lines for cooling (U.S. Pat. No. 4,638,674).

Process gases and liquids have been sampled directly on production lines, using syringes, special bags or rigid metal canisters.

All of these techniques, however, fall short in one or more of the following circumstances: when the sample or the process fluid from which the sample is taken must not be contaminated, when ultra-trace analysis of gases with very low concentrations of impurities is necessary, when a small sample is desirable, when consistent multiple injections (subsamples) from a single sample are needed and when it is necessary to transfer the sample to a remote site for analysis.

Therefore, it is an object of this invention to provide an apparatus for sampling fluids without introduction of contaminants.

It is a further object of this invention to provide an apparatus for sampling fluids with very low concentrations of tested-for substances for ultra-trace analyses.

It is another object of this invention to provide an apparatus for obtaining small samples of fluids.

It is yet another object of this invention to provide an apparatus for dispensing identical subsamples of fluid samples. It is still another object of this invention to provide an apparatus for transferring fluid samples from sampling locations to analysis locations without contamination.

It is also an object of this invention to provide a process for sampling gases without introduction of contaminants.

Additional objects, advantages and novel features of the invention will be set forth, in part, in the description which follows, and, in part, will become apparent to those skilled in the art upon examination of the following or may be learned by practice of the invention. The objects and advantages of the invention may be realized and attained by means of the instrumentalities and combinations particularly pointed out in the appended claims.

DISCLOSURE OF INVENTION

To achieve the foregoing and other objects, and in accordance with the purposes of the present invention, as embodied and broadly described herein, there has been invented an apparatus for fluid sampling. The apparatus comprises:

a bellows having a first end and a second end; said bellows having a plunger attached to said first end of said bellows and an uptake tube attached to said second end of said bellows whereby said bellows is compressed or extended by operation of said plunger; said uptake tube has a valve thereon whereby closing said valve prevents exchange of fluid within said bellows and the portion of said uptake tube between said valve and said bellows with fluid external to said bellows and portion of said uptake tube between said bellows and said valve.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

BEST MODES FOR CARRYING OUT THE INVENTION

Figure 1:
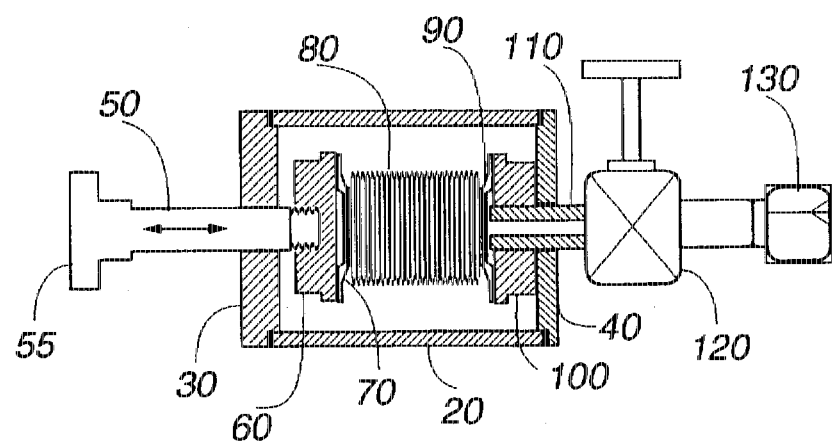
FIG. 1 is a sectional view of an embodiment of the fluid sampling apparatus of this invention.

We have discovered that incorporation of a bellows in a sampling syringe with a close-off valve eliminates ingress of contaminants, permits precise replication of sample amounts and compression of multiple sample injections, and enables sampling for remote off-site analysis.

The bellows is attached at its closed end to a plunger or handle of some sort so that operating the plunger expands or compresses the bellows.

The bellows can be any of a very large range of sizes. A bellows as small or smaller than one cubic centimeter could be useful for collecting very small samples. For large industrial operations bellows measured in cubic meters are contemplated. Generally, bellows size is controlled by the size of samples desired, and, to some extent, by the amount of pressure of the fluid to be sampled.

Surrounding the bellows is a housing which can be either an open or closed structure which serves as a support frame for the sampling apparatus or as a referent structure for operation of the plunger.

The housing is large enough to accommodate the bellows in its fully extended position as well as attachments to the bellows of the plunger and an uptake-injection tube. For situations where there will be a lot of pressure in the bellows, the housing can be sized so as to prevent bulging of the bellows in sideways directions by providing support to the sides of the bellows. The housing as a practical matter is preferably not so large as to be difficult to transport or handle and get into areas from which samples are to be taken.

At one end of the housing is a back plate which has an opening to accommodate the plunger. This opening is large enough to permit movement of the plunger but not so large as to allow undesirable free-play in movement of the plunger. Any other sort of framework, including an open framework, may serve as the back plate.

At the other end of the housing is a front plate with an opening through which an uptake-injection tube passes. The uptake tube is generally welded, soldered or otherwise attached in a fixed position in the front plate of the housing. As with the back plate, any other sort of framework, including an open framework, may serve as the front plate, so long as it securely holds the uptake tube in position.

Alternatively, the end of the bellows opposite the plunger end may be attached directly to the interior of the front plate of the housing with the uptake tube attached to the exterior face of the front plate of the housing. The uptake tube in this alternative embodiment is aligned with a hole through the housing and the opening in the end of the bellows and is attached in an airtight manner.

The end of the uptake tube opposite the bellows can have fittings for connecting the uptake tube to analytical devices such as gas chromatographs, infrared spectrometers, or residual gas analyzers. Fittings for connecting the uptake tube to various sorts of gas or liquid processes or containers which would hold gas to be sampled can be on the end of the uptake tube opposite the bellows or adapted thereto. These include, but are not limited to, traditional syringe needles, threaded fittings, vacuum fittings, metal seal fittings and valve manifolds.

When a tubular cylinder is used as the housing, one or both ends (front plate and back plate) of the housing may be removeably mounted to the housing cylinder walls to facilitate inspection and repair of the sampling apparatus.

Housings for the invention sampling apparatuses can be made from any material which is structurally sound enough to be operated in various environments without stress cracking, breaking, corroding, bending or otherwise mechanically failing. The material for the housing should be sufficiently rigid and strong to withstand the forces of sample collection and analysis. Generally presently preferred is stainless steel.

The bellows and uptake tube can be made of any material which is completely impermeable to the contaminant to be avoided, will structurally support the bellows action, and will be inert to the fluids being sampled. When the contaminant to be avoided is air, a material which is impermeable to oxygen and nitrogen, such as stainless steel is generally preferred. Other metals are also useful for bellows and uptake tubes on apparatuses for some sampling applications. Passivation of the bellows and uptake tube is one of the strategies employed to insure accuracy of sampling and analysis.

The plunger is attached to the closed end of the bellows by means of a weld, solder, adhesive, clips, threads or another mechanical grasping method. Alternatively, another means of compressing the bellows, such as an inflatable apparatus, can be used to compress and release the bellows.

The plunger or back bellows flange has a shoulder inside of the housing or some means of limiting outward travel of the plunger to the desired fullest extension of the bellows. The plunger or housing also may have some lock, projection or shoulder for limiting travel into the housing to the desired most compressed position of the bellows. There may also be incremental stop mechanisms and/or scales along the plunger as needed for positioning the plunger to provide incremental bellows capacities. Hardware of a variety of types can be mounted on the housing to provide a reference plane for incremental plunger positions and to move the plunger incrementally to compress or extend the bellows incrementally. Various locking devices can be used to hold the plunger in position.

The plunger is made from any material which is structurally sound enough to be operated in various environments without stress cracking, breaking, corroding, bending or otherwise mechanically failing. Generally presently preferred for applications such as 0 to 10 psi helium sampling are plungers made from aluminum.

The size plunger needed will depend upon the size of the bellows to be operated by the plunger and upon the material from which the plunger is made. Generally a plunger large enough to easily permit manipulation by hand and small enough to enable use of the sampling apparatus in small areas is preferred. A handle can be attached to the end of the plunger opposite the end which is attached to the bellows for convenience in using the device manually. Or, the end of the plunger itself may have a flange shape or shoulder for this purpose.

The plunger can be operated by hand or mechanically with a purely mechanical device or with computerized equipment programmed to move the plunger specified distances at specified intervals.

FIG. 1 shows one embodiment of the invention sampling apparatus. With reference to FIG. 1, a bellows 80 is enclosed by a cylindrical housing 20 having an aperture in one end through which a plunger 50 passes. The plunger 50 has a handle 55 on the end exterior to the housing 20. The end of the plunger 50 inside the housing 20 is threaded into, but not through, a back bellows flange 60 which is attached to the back bellows cuff 70 of the bellows 80. The end of the bellows 80 opposite the end attached via the back bellows cuff 70 to the back bellows flange 60 into which the plunger 50 is threaded is attached to a front bellows cuff 90 which is mounted on the front bellows flange 100. The front bellows flange 100 is mounted to the inside of a housing front plate 40 in such a way that the uptake tube 110 on the aperture in the end of the bellows 80 is positioned and attached so as to pass through the front bellows flange 100 and the housing front plate 40. There is a valve 120 on the uptake tube 110 exterior to the housing front plate 40. The portion of the uptake tube 110 extending beyond the valve 120 may be equipped with a vacuum fitting 130 or other connection device. Alternatively, the end of the uptake tube opposite the bellows can be equipped with a needle for pulling samples through a septum, rubber membrane, or pierceable bag; or with fittings of other sorts for attaching the uptake tube to process sample ports, containers holding fluids to be sampled, or a valve manifold.

Figure 2:
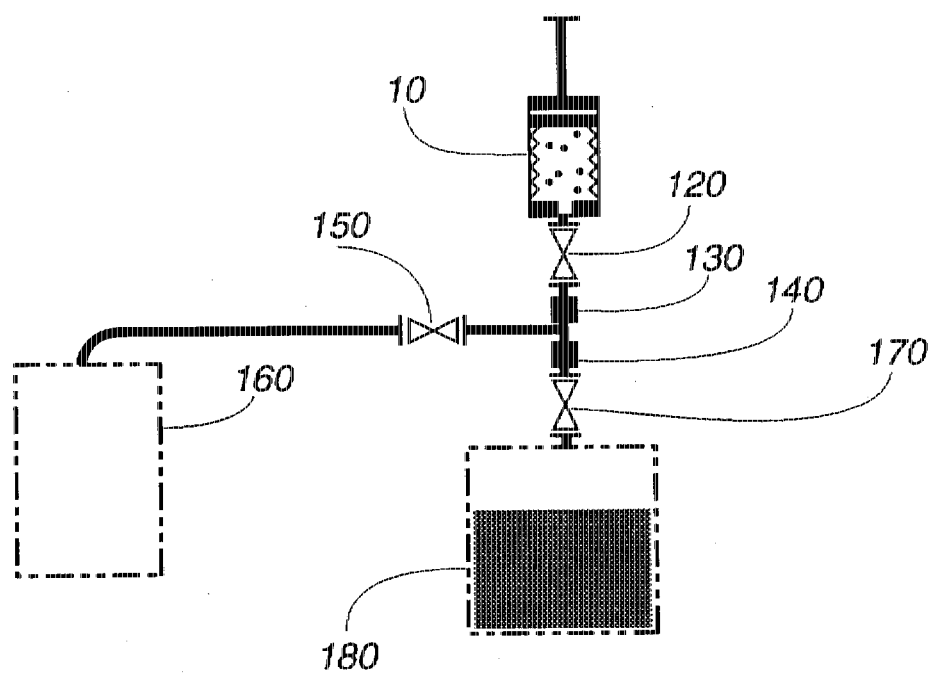
FIG. 2 is a schematic diagram of a fluid sampling system using the invention sampling apparatus.

FIG. 2 is an example of how the invention sampling apparatus can be set up for sampling a process. With reference to FIG. 2, the invention sampling apparatus 10 is connected with a vacuum fitting or other connection to a process system 180 to be sampled via a tee joint having a valve 150 for closing off the leg of the tee which goes to a vacuum pump 160, and a valve 170 for closing off the leg of the tee connected to the process being sampled 180 (test manifold). The second leg of the tee is attached at connection 130 to the test manifold on the process to be tested.

Still with reference to FIG. 2, with the valves on the uptake tube 110 and on the leg of the tee connecting it to the vacuum 160 open, the tee joint, uptake tube 110 and bellows 80 are evacuated of contaminants by operation of the vacuum pump 160. The system can be flushed with inert gas or the system can be evacuated with a vacuum attached to the third leg of the tee joint. Alternatively, the bellows 80 could be pre-evacuated and the inert gas flush or vacuum used only to evacuate the portion of the uptake tube 110 on the opposite side of the valve 120 which closes it off from the bellows and the tee joint. If the bellows 80 has been used to sample liquids, the system may need to be flushed with liquids before using an inert gas flush or vacuum to evacuate the system.

After the tee joint, uptake tube 110 and bellows 80 are evacuated, valve 150 on the third leg of the tee which is connected to the source of inert gas to flush the system or vacuum to evacuate the system is closed. Valve 170 is opened allowing the fluid to be sampled to enter the tee. The valve on the uptake tube 110 is then opened and closed to capture the fluid sample in the bellows which is extended the length necessary to accommodate the volume of sample desired. If the bellows is not already extended to the length necessary to accommodate the volume of sample desired before the fluid sampling apparatus is attached to the test manifold and the valves opened, then, once the valves are opened the plunger is withdrawn to the desired extent. This can be a better method of collecting liquid samples.

After the time necessary for the fluid to either enter the bellows by diffusion (in the case in which the bellows was extended prior to opening the test manifold valve) or after the plunger is withdrawn the desired extent to pull the sample into the bellows, the valves to the test manifold and on the uptake tube are closed.

If the fluid being sampled is toxic, hazardous, radioactive or otherwise environmentally objectionable, the tee joint could be evacuated once again after the sample is collected before the sampling apparatus is disconnected from the tee and/or the tee is disconnected from the process conduit, container, or apparatus from which the sample is being drawn to prevent escape of any of the fluid into the atmosphere.

The valve 120 on the uptake tube 110 isolates the sample fluid from contamination during transport and attachment to whatever analytical devices are to be used.

The bellows can be compressed a chosen amount to obtain the specific pressure of the sample desired for analysis.

One or more precisely measured units of the fluid to be analyzed can be dispensed from the sampling apparatus by compression of the bellows by operation of the plunger.

Figure 3:
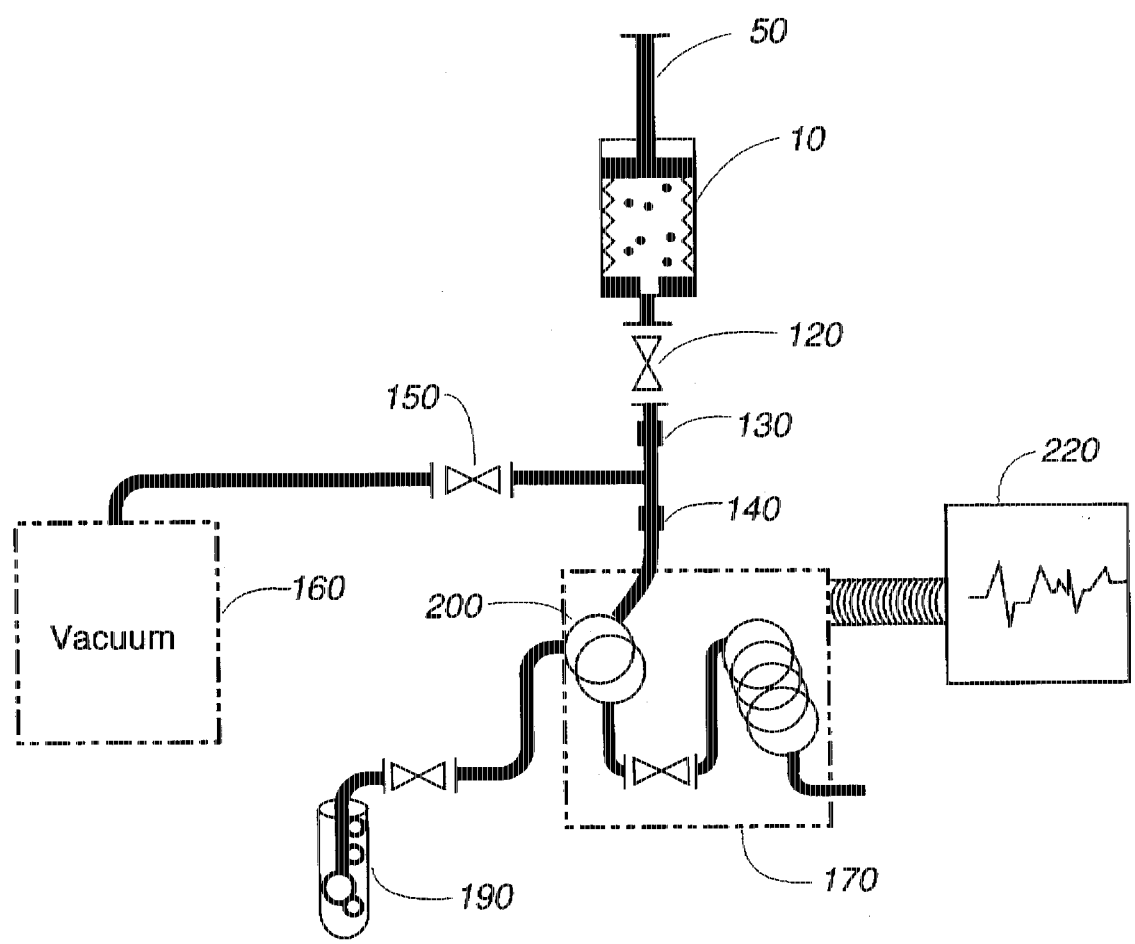
FIG. 3 is a schematic diagram of an fluid analysis system adapted for use with a gas chromatograph using the invention sampling apparatus.

FIG. 3 shows an example of how the sampling apparatus of this invention can be set up for analyzing samples which have been collected. With reference to FIG. 3, the sampling apparatus 10 is connected with a vacuum fitting or other connection 130 to the analytical device 170 (in this example, a gas chromatograph) via a tee joint. A valve 120 isolates the sample fluid from contamination during transport and attachment to the chromatograph or other analytical device 170.

A vacuum producing means 160 is attached to another leg of the tee joint with a second valve 150 between the vacuum 160 and the tee joint.

A vacuum fitting 140 or other connection attaches the tee to the gas chromatograph or other analytical device 170.

The vacuum system 160 clears the sample loops 200 and the tee joint. The valve 150 is then closed and the valve 120 on the uptake tube 110 is opened.

Then pressure is regulated to the desired number of atmospheres with the sampling device plunger 50 and a vent 190 to the atmosphere from the chromatograph 170 before the sample is analyzed.

The plunger 50 can be operated to compress the sample if a more concentrated sample is needed for certain analytical procedures.

Samples can be taken with the invention sampling apparatus with introduction of less than 1 ppm of air. The invention sampling apparatus is excellent for sampling gases with very low concentrations of the substances being tested for because of the lack of contaminants added during sampling and because the sample can easily be concentrated by operation of the plunger.

The invention sampling apparatus can be used to take very small samples with excellent control of the size and compression of the sample. No additional instruments are required for pressurizing the samples since the bellows action can be used to pressurize the samples in accurately controllable increments. These features make the sampling apparatus of this invention particularly suitable for replicating sample sizes and concentrations when multiple identical samples of the same fluid are needed. Additionally, samples can be analyzed without the use of built-in pressure sensors because the sample fluid can be set to exactly 1 atmosphere by using the bellows and system vent together.

Use of the invention sampling apparatus enables on-site collection of fluid samples for off-site analysis since the sampling apparatus can hold the samples free of contamination at constant pressures for long periods of time. The samples can be held in the sampling apparatuses of this invention for 30 days or longer.

The sampling apparatuses of this invention can be particularly useful for bioscience applications. For example, the sampling apparatus has been used for sampling the gaseous environment of microbial cultures to demonstrate that the microbial environment was anoxic.

The sampling apparatuses of this invention are also particularly useful for sampling toxic, hazardous or otherwise difficult to handle gases. For example, the sampling apparatus is particularly useful for taking headspace samples from drums of radioactive material because once the sample is closed off from the atmosphere with the valve on the uptake tube, the tee joint and the rest of the collection connections can be evacuated of the material being sampled before any valves or connections which would release gas to the atmosphere are opened.

EXAMPLE I

A sampling apparatus was constructed in the embodiment shown in FIG. 1. The housing and bellows flanges of the sampling apparatus were made out of 304 stainless steel and the bellows was made from AM 350 stainless steel.

The housing was a 1.675" long cylinder with an outside diameter of 1½" and wall thickness of 0.065". A plunger with a 1 3/16" long shaft had the terminal 3/16" threaded with ¼–20 threads. A ⅜" diameter, 3/16" long shoulder topped by a ¾" diameter, 3/16" long handle portion was on the end of the plunger opposite the threaded end of the plunger.

The plunger was attached to a circular ¼" thick, ¾" diameter plate. The center of the plate was drilled only to a depth of 3/16" to accommodate the end of the plunger to be attached by means of the drilled and threaded hole without drilling the hole all the way through the plate.

The plate was welded onto the closed end of a 0.540" inside diameter, 1.05" long bellows which was compressible to a length of 0.30". The open end of the bellows was welded onto a flange which was welded into the inside of the end of the housing opposite the end through which the plunger was positioned.

Extending from the open end of the bellows was an uptake tube with an integral valve connected to the interior of the bellows. The uptake tube was positioned through a ¼" diameter hole in the center of the front flange and the end of the housing along the axis of the cylindrical housing. The uptake tube extended ½" beyond the end of the housing, where the uptake tube was fluidly connected to a Nupro™ bellows valve.

The bellows portion of the sampling apparatus was a welded bellows commercially available from MDC. The bellows had 1.070" outside diameter end plates of 304 stainless steel and a bellows portion made from AM 350 stainless steel. The bellows had an outside diameter of 1.030", an inside diameter of 0.540", a fully extended length of 1.05" and a fully compressed length of 0.30".

The nominal bellows volume was 5 cc which was compressible to 1 cc.

The valve on the uptake tube was connected to a T-section.

A vacuum of less than 5 microns was applied.

Samples of standard gas consisting of 506 ppm methane in helium which was free of the presence of oxygen and nitrogen were taken from a prototype sampling manifold. Each of the samples showed an identical amount (506 ppm) of the methane.

After each of the samples was taken the manifold was evacuated and backfilled with a new charge of the standard gas. The purpose of the helium flushes was to determine in how short a time a substantially zero oxygen level in the sampling apparatus could be achieved. It was determined that a substantially zero oxygen level could be achieved in under 2 minutes.

For comparison purposes, identical samples of the same oxygen and nitrogen free methane were taken with a Dynatech Pressure Lok™ A-2 Gas sampling syringe with a 0 to 10 cc volume sampling device and with a Hamilton Gastite™ 1010C sampling syringe with a 0 to 10 cc volume. The Dynatech Pressure Lok™ A-2 Gas sampling syringe was equipped with a plastic plunger seal and had needle and septum connections. The Hamilton Gastite™ 1010C sampling syringe was equipped with a plastic plunger seal and had plastic face seals for connections with Hamilton™ HV3-3 vacuum valves.

These features were in contrast with the invention sampling device which had a welded stainless steel plunger seal and metal gasket connections.

The amounts of air that leaked into the sampling syringes while the samples were being drawn are shown in Table 1. A hundred ppm of air will introduce unacceptable contamination to the process gas and mask the analysis results.

TABLE 1

Amounts of Air Drawn into Samples

| Sampling Device | Contamination Present per 5-cm³ Sample |
|---|---|
| Dynatech Pressure Lok™ A-2 | >100 ppm |
| Hamilton Gastite™ 1010C | >100 ppm |
| Invention Apparatus | <1 ppm |

These results shown in Table 1 demonstrate that the invention sampling apparatus virtually eliminates contamination by air in the sampling and analysis process.

While the apparatuses and processes of this invention have been described in detail for the purpose of illustration, the inventive apparatuses and processes are not to be construed as limited thereby. This patent is intended to cover all changes and modifications within the spirit and scope thereof.

INDUSTRIAL APPLICABILITY

The sampling apparatuses of this invention can be used for any application requiring sampling of gases for analysis, quality control, historical preservation, or other purposes. Applications include sampling from inert atmospheres such as those in gloveboxes, sampling oxygen-sensitive chemistry enclosures, sampling headspace gas in containers of chemicals, and bioscience applications including sampling of gaseous environments of microbial cultures. The sampling apparatuses of this invention are useful for off-line analysis of process gases in microelectronics manufacturing, chemical and pharmaceuticals manufacturing and the processing of reactive metals.

The invention sampling apparatuses can be used to enable on-site collection of gas samples for analysis at another location, thus eliminating the need for on-line analytical instrumentation. This makes mobile analytical services an appropriate use for the invention sampling apparatuses.

The sampling apparatuses of this invention are useful for reliably and accurately dispensing multiple identical-sized injections of the same sample having the same concentrations.

What is claimed is:

1. A process for sampling fluids comprising:
   (a) providing a bellows having a first end and a second end; said bellows having a plunger attached to said first end of said bellows and an uptake tube attached to said second end of said bellows whereby said bellows is compressed or extended by operation of said plunger; said uptake tube having a valve thereon whereby closing said valve prevents exchange of fluid within said bellows and the portion of said uptake tube between said valve and said bellows with fluid in portion of said uptake tube on opposite side of said valve from said bellows; thereafter
   (b) removing contaminants from said bellows and said uptake tube by applying a vacuum thereto; thereafter
   (c) closing said valve on said uptake tube; thereafter
   (d) connecting said uptake tube to a container of fluid to be sampled; thereafter
   (e) removing contaminants from said portion of said uptake tube on side opposite said valve from said bellows by applying a vacuum thereto; thereafter
   (f) opening said valve on said uptake tube; and
   (g) after transfer of said fluid to be sampled into said bellows, closing said valve on said uptake tube.

2. A process as recited in claim 1 wherein said fluid to be sampled is drawn into said bellows by operation of said plunger.

3. A process for introducing samples to an analyzer comprising:
   (a) providing a bellows having a first end and a second end; said bellows having a plunger attached to said first end of said bellows and an uptake tube attached to said second end of said bellows whereby said bellows is compressed or extended by operation of said plunger; said uptake tube having a valve thereon whereby closing said valve prevents exchange of fluid within said bellows and the portion of said uptake tube between said valve and said bellows with fluid in portion of said uptake tube on opposite side of said valve from said bellows, said bellows having therein a sample to be analyzed;

(b) connecting said uptake tube to an analytical instrument;

(c) removing contaminants from said portion of said uptake tube on side opposite said valve from said bellows by applying a vacuum thereto;

(d) adjusting pressure of said sample; and (e) opening said valve on said uptake tube.

* * * * *